(12) United States Patent
Themens

(10) Patent No.: US 8,900,608 B2
(45) Date of Patent: Dec. 2, 2014

(54) COSMETIC COMPOSITION COMPRISING AT LEAST TWO EMULSIFYING SILICONE ELASTOMERS

(75) Inventor: Agnès Themens, Bourg la Reine (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 11/480,391

(22) Filed: Jul. 5, 2006

(65) Prior Publication Data

US 2007/0020217 A1    Jan. 25, 2007

Related U.S. Application Data

(60) Provisional application No. 60/712,828, filed on Sep. 1, 2005.

(30) Foreign Application Priority Data

Jul. 4, 2005    (FR) ..................................... 05 52022

(51) Int. Cl.
| | | |
|---|---|---|
| A61K 8/89 | (2006.01) | |
| A61K 8/894 | (2006.01) | |
| A61K 8/34 | (2006.01) | |
| A61K 8/58 | (2006.01) | |
| A61K 8/891 | (2006.01) | |
| A61Q 1/02 | (2006.01) | |

(52) U.S. Cl.
CPC .................. *A61K 8/894* (2013.01); *A61K 8/345* (2013.01); *A61K 8/585* (2013.01); *A61K 8/891* (2013.01); *A61Q 1/02* (2013.01)
USPC ........................................ 424/401; 424/70.12

(58) Field of Classification Search
CPC ....... A61K 8/345; A61K 8/585; A61K 8/891; A61K 8/894; A61Q 1/02
USPC .............................................. 424/401, 70.12
See application file for complete search history.

(56) References Cited

U.S. PATENT DOCUMENTS

| | | | |
|---|---|---|---|
| 5,236,986 A | 8/1993 | Sakuta | |
| 5,412,004 A | 5/1995 | Tachibana et al. | |
| 5,811,487 A | 9/1998 | Schulz, Jr. et al. | |
| 5,837,793 A | 11/1998 | Harashima et al. | |
| 6,103,250 A | 8/2000 | Brieva et al. | |
| 6,171,581 B1 | 1/2001 | Joshi et al. | |
| 2002/0022040 A1 | 2/2002 | Robinson et al. | |
| 2002/0058054 A1* | 5/2002 | Arnaud ........................ | 424/401 |
| 2005/0220728 A1* | 10/2005 | Kanji et al. ..................... | 424/59 |
| 2006/0034875 A1 | 2/2006 | Nakanishi et al. | |
| 2006/0263310 A1* | 11/2006 | Elliott et al. .................... | 424/63 |

FOREIGN PATENT DOCUMENTS

| | | |
|---|---|---|
| EP | 0 293 795 B1 | 12/1988 |
| EP | 0 295 886 81 | 12/1988 |
| EP | 0 813 403 B1 | 12/1997 |
| EP | 1 086 683 B1 | 3/2001 |
| WO | WO 2004/024798 A1 | 3/2004 |

OTHER PUBLICATIONS

French Search Report for FR 05 52022, dated Mar. 30, 2006.
Office Action issued Feb. 7, 2012 in Japan Application No. 2006-183764 (With English Translation).
Office Action issued Apr. 16, 2013 in Japanese Application No. 2006-183764 (English Translation).

\* cited by examiner

*Primary Examiner* — Johann R Richter
*Assistant Examiner* — Courtney Brown
(74) *Attorney, Agent, or Firm* — Oblon, Spivak, McClelland, Maier & Neustadt, L.L.P.

(57) ABSTRACT

The disclosure relates to a cosmetic composition in the form of a water-in-oil emulsion comprising at least two different emulsifying silicone elastomers, the emulsifying elastomers being present in an amount of at least 3% by weight relative to the total weight of the composition. The disclosure also relates to the use of such a composition to obtain makeup that is comfortable and/or that has no tacky feel and/or that spreads easily.

49 Claims, No Drawings

COSMETIC COMPOSITION COMPRISING AT LEAST TWO EMULSIFYING SILICONE ELASTOMERS

This application claims benefit of U.S. Provisional Application No. 60/712,828, filed Sep. 1, 2005, the contents of which are incorporated herein by reference. This application also claims benefit of priority under 35 U.S.C. §119 to French Patent Application No. FR 05 52022, filed Jul. 4, 2005, the contents of which are also incorporated herein by reference.

The present disclosure relates to a cosmetic composition in the form of a water-in-oil emulsion comprising emulsifying silicone elastomers. The composition may be a makeup or care composition for keratin materials such as the skin, the lips or the hair. In at least one embodiment, the keratin material is the skin. The present disclosure also relates to a process for making up or caring for human keratin materials.

Makeup compositions, such as foundations, may be in the form of anhydrous compositions or emulsions, and may have varied textures ranging from fluid to solid.

Emulsions with an oily continuous phase, or water-in-oil emulsions, are often used on account of their good adhesion to the epidermis, their protective nature and their ability to form a water-impermeable film. The makeup obtained may be comfortable and may not dry out the skin.

However, these emulsions give a greasy feel that makes them relatively unappealing, such as for users with a tendency towards greasy skin.

To obtain an emulsion having a thick texture, it is known practice to use non-emulsifying silicone elastomers, as described in European Patent Application No. EP 0 813 403.

However, when these non-emulsifying elastomers are used in large amount, for example, greater than 3% by weight, the composition becomes too thick and even has a compact appearance. The composition is difficult to spread on the skin and the applied makeup is not uniform.

Thus, there is a need for new care or makeup products with novel textures.

Accordingly, the present disclosure relates to makeup or care compositions that can be spread easily on the skin and that have a thick texture that may remain creamy on application.

Such a composition may have a creamy texture and a soft feel when taken up with the fingers. When applied to the skin, the composition may stretch well when spread out and may give a soft, fondant sensation.

The present inventors have discovered that by combining, in a water-in-oil emulsion, at least two different emulsifying silicone elastomers, it is possible to obtain a composition with a thick, creamy texture that may spread easily on the skin without giving a greasy or tacky feel.

Thus, one aspect of the present disclosure relates to a cosmetic composition in the form of a water-in-oil emulsion comprising at least two different emulsifying silicone elastomers, the emulsifying elastomers being present in an amount greater than or equal to 3% by weight relative to the total weight of the composition.

Another aspect of the present disclosure relates to a cosmetic (non-therapeutic) process for making up or caring for keratin materials, comprising the application to the keratin materials of a composition as defined above.

A further aspect of the present disclosure relates to the use of a composition as defined above to obtain makeup that is comfortable and/or that has no tacky feel and/or that spreads easily.

Emulsifying Elastomers

The composition according to the present disclosure comprises at least two different emulsifying silicone elastomers.

In the context of the present disclosure, the term "emulsifying silicone elastomer" means a silicone elastomer comprising at least one hydrophilic chain.

The emulsifying silicone elastomer may be chosen from polyoxyalkylenated silicone elastomers.

The polyoxyalkylenated silicone elastomers are cross-bonded organopolysiloxanes that may be obtained by a crosslinking addition reaction of diorganopolysiloxane comprising at least one hydrogen bonded to silicon and of a polyoxyalkylene comprising at least two ethylenically unsaturated groups.

In at least one embodiment, the polyoxyalkylenated cross-bonded organo-polysiloxanes are obtained by a crosslinking addition reaction of (A1) diorganopolysiloxane comprising at least two hydrogens each bonded to a silicon, and (B1) polyoxyalkylene comprising at least two ethylenically unsaturated groups, optionally in the presence of (C1) a platinum catalyst, as described, for example, in U.S. Pat. No. 5,236,986 and U.S. Pat. No. 5,412,004.

In at least one further embodiment, the organopolysiloxanes are obtained by reaction of polyoxyalkylene (for example, polyoxyethylene and/or polyoxypropylene) comprising dimethylvinylsiloxy end groups and of methylhydrogenopolysiloxane comprising trimethylsiloxy end groups, in the presence of a platinum catalyst.

In at least one embodiment, compound (A1) comprises organic groups bonded to the silicon atoms that may be chosen from alkyl groups comprising from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

In at least one embodiment, compound (A1) is chosen from methylhydrogeno-polysiloanes comprising trimethylsiloxy end groups, dimethylsiloxane-methylhydrogensiloxane copolymers comprising trimethylsiloxy end groups, dimethylsiloxane-methylhydrogenosiloxane cyclic copolymers, and dimethylsiloxane-methylhydrogenosiloxane-laurylmethylsiloxane copolymers comprising trimethylsiloxy end groups.

Compound (C1) is the crosslinking reaction catalyst, and may be chosen from, for example, chloroplatinic acid, chloroplatinic acid-olefin complexes, chloroplatinic acid-alkenylsiloxane complexes, chloroplatinic acid-diketone complexes, platinum black and platinum on a support.

In at least one embodiment, the polyoxyalkylenated silicone elastomers are formed from divinyl compounds, such as polyoxyalkylenes comprising at least two vinyl groups, reacting with Si—H bonds of a polysiloxane.

The polyoxyalkylenated silicone elastomers according to the present disclosure may be mixed with at least one hydrocarbon-based oil and/or one silicone oil to form a gel. In these gels, the polyoxyalkylenated elastomers are in the form of non-spherical particles.

Polyoxyalkylenated elastomers are described, for example, in U.S. Pat. No. 5,236,986, U.S. Pat. No. 5,412,004, U.S. Pat. No. 5,837,793 and U.S. Pat. No. 5,811,487, the contents of which are incorporated by reference.

Polyoxyalkylenated silicone elastomers that may be used in at least one embodiment of the present disclosure include those sold under the names KSG-21, KSG-20, KSG-30, KSG-31, KSG-32, KSG-33, KSG-210, KSG-310, KSG-320, KSG-330, KSG-340 and X-226146 by the company Shin-Etsu, and DC9010 and DC9011 by the company Dow Corning.

The emulsifying silicone elastomers may also be chosen from polyglycerolated silicone elastomers.

The polyglycerolated silicone elastomers are crossbonded elastomeric organopolysiloxanes that may be obtained by a crosslinking addition reaction of diorganopolysiloxane comprising at least one hydrogen bonded to silicon and of polyglycerolated compounds containing ethylenically unsaturated groups, optionally in the presence of a platinum catalyst.

In at least one embodiment, the crossbonded elastomeric organopolysiloxanes are obtained by a crosslinking addition reaction of (A) diorganopolysiloxane comprising at least two hydrogens each bonded to a silicon, and (B) glycerolated compounds comprising at least two ethylenically unsaturated groups, optionally in the presence of (C) a platinum catalyst.

In at least one embodiment, the organopolysiloxanes are obtained by reaction of a polyglycerolated compound comprising dimethylvinylsiloxy end groups and of methylhydrogenopolysiloxane comprising trimethylsiloxy end groups, in the presence of a platinum catalyst.

Compound (A) is the base reagent for the formation of elastomeric organopolysiloxane and the crosslinking is performed by an addition reaction of compound (A) with compound (B) in the presence of the catalyst (C).

In at least one embodiment, compound (A) is an organopolysiloxane comprising at least 2 hydrogen atoms bonded to different silicon atoms in each molecule.

Compound (A) may have any molecular structure, such as, for example, a linear chain or branched chain structure or a cyclic structure.

Compound (A) may have a viscosity at 25° C. ranging from 1 to 50,000 centistokes, and may be chosen in order to have good miscibility with compound (B).

In at least one embodiment, compound (A) comprises organic groups bonded to the silicon atoms that may be chosen from alkyl groups comprising from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. In at least one further embodiment, the organic groups are chosen from methyl, phenyl and lauryl groups.

In at least one embodiment, compound (A) is chosen from methylhydrogeno-polysiloxanes comprising trimethylsiloxy end groups, dimethylsiloxane-methylhydrogenosiloxane copolymers comprising trimethylsiloxy end groups, dimethylsiloxane-methylhydrogenosiloxane cyclic copolymers, and dimethylsiloxane-methylhydrogenosiloxane-laurylmethylsiloxane copolymers comprising trimethylsiloxy end groups.

Compound (B) may be a polyglycerolated compound of formula (B') below:

(B')

wherein m is an integer ranging from 2 to 6, n is an integer ranging from 2 to 200, such as, for example, from 2 to 100, from 2 to 50, from 2 to 20, from 2 to 10, or from 2 to 5, and in at least one embodiment, n is equal to 3; Gly is chosen from:

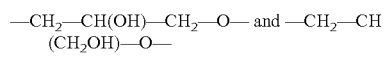

In at least one embodiment, the sum of the number of ethylenic groups per molecule of compound (B) and the number of hydrogen atoms bonded to silicon atoms per molecule of compound (A) is at least 4.

In at least one embodiment of the present disclosure, compound (A) is added in an amount such that the molar ratio between the total amount of hydrogen atoms bonded to silicon atoms in compound (A) and the total amount of all the ethylenically unsaturated groups in compound (B) ranges from 1/1 to 20/1.

Compound (C) is the crosslinking reaction catalyst, and in at least one embodiment, may be chosen from chloroplatinic acid, chloroplatinic acid-olefin complexes, chloroplatinic acid-alkenylsiloxane complexes, chloroplatinic acid-diketone complexes, platinum black and platinum on a support.

In at least one embodiment, the catalyst (C) is added in an amount ranging from 0.1 to 1000 parts by weight, such as, for example, from 1 to 100 parts by weight, as clean platinum metal per 1000 parts by weight of the total amount of compounds (A) and (B).

Polyglycerolated silicone elastomers according to the present disclosure may be mixed with at least one hydrocarbon-based oil and/or one silicone oil to form a gel. In these gels, polyglycerolated elastomers are often in the form of non-spherical particles.

Such elastomers are described, for example, in International Patent Application No. WO 2004/024798.

Polyglycerolated silicone elastomers that may be used according to at least one embodiment of the present disclosure include those sold under the names KSG-710, KSG-810, KSG-820, KSG-830 and KSG-840 by the company Shin-Etsu.

According to at least one embodiment, at least one of the emulsifying silicone elastomers is a polyglycerolated elastomer.

According to at least one embodiment, the emulsion according to the present disclosure comprises at least one polyoxyalkylenated elastomer and at least one polyglycerolated elastomer.

According to at least one embodiment of the present disclosure, the emulsifying silicone elastomers are present in the composition in an amount of at least 3% by weight, such as from 3% to 15% by weight, at least 3.5% by weight, such as from 3.5% to 10% by weight, or at least 4% by weight, such as from 4% to 7% by weight, relative to the total weight of the composition.

According to at least one embodiment of the present disclosure, each emulsifying elastomer is present in the composition in an amount of at least 1.5% by weight, such as from 1.5% to 5% by weight, relative to the total weight of the composition.

In at least one embodiment, the emulsion comprises at least one polyoxyalkylenated elastomer in an amount comprising of at least 1.5% by weight, such as from 1.5% to 5% by weight, relative to the total weight of the composition, and a polyglycerolated elastomer in an amount comprising at least 1.5% by weight, such as from 1.5% to 5% by weight, relative to the total weight of the composition.

Another aspect of the present disclosure relates to a cosmetic composition in the form of a water-in-oil emulsion comprising:
i) at least 1.5% by weight, relative to the total weight of the composition, of a polyoxyalkylenated emulsifying silicone elastomer;
ii) at least 1.5% by weight, relative to the total weight of the composition, of a polyglycerolated emulsifying silicone elastomer;

iii) at least 20% by weight, relative to the total weight of the composition, of water;
iv) at least one volatile oil;
v) at least 5% by weight, relative to the total weight of the composition, of at least one water-miscible organic solvent chosen from glycols and polyols; and
vi) at least 5% by weight, relative to the total weight of the composition, of at least one dyestuff, wherein the composition has a viscosity ranging from 10 Pa·s to 300 Pa·s for a shear of 1 s$^{-1}$.

Additional Non-Emulsifying Elastomers

In addition to emulsifying elastomers, the composition according to the present disclosure may comprise non-emulsifying elastomers.

In the context of the present disclosure, the term "non-emulsifying" silicone elastomers means organopolysiloxane elastomers not containing a hydrophilic chain, such as polyoxyalkylene or polyglycerolated chains.

Non-emulsifying silicone elastomers are elastomeric crossbonded organopolysiloxanes that may be obtained by a crosslinking addition reaction of diorganopolysiloxane comprising at least one hydrogen bonded to silicon and of diorganopolysiloxane comprising ethylenically unsaturated groups bonded to silicon, optionally in the presence of a platinum catalyst; or by dehydrogenation crosslinking coupling reaction between a diorganopolysiloxane comprising hydroxyl end groups and a diorganopolysiloxane comprising at least one hydrogen bonded to silicon, optionally in the presence of an organotin compound; or by a crosslinking coupling reaction of a diorganopolysiloxane comprising hydroxyl end groups and of a hydrolysable organopolysilane; or by thermal crosslinking of organopolysiloxane, optionally in the presence of an organoperoxide catalyst; or by crosslinking of organopolysiloxane via high-energy radiation such as gamma rays, ultraviolet rays or an electron beam.

In at least one embodiment, elastomeric crossbonded organopolysiloxanes are obtained by a crosslinking addition reaction of (A2) diorganopolysiloxane comprising at least two hydrogens each bonded to a silicon, and of (B2) diorganopolysiloxane comprising at least two ethylenically unsaturated groups bonded to silicon, optionally in the presence of (C2) a platinum catalyst, as described, for example, in European Patent Application No. EP-A-0 295 886.

In at least one embodiment of the present disclosure, organopolysiloxanes are obtained by reaction of dimethylpolysiloxane comprising dimethylvinylsiloxy end groups and of methylhydrogenopolysiloxane comprising trimethylsiloxy end groups, in the presence of a platinum catalyst.

Compound (A2) is the base reagent for the formation of elastomeric organopolysiloxane, and the crosslinking is performed by an addition reaction of compound (A2) with compound (B2) in the presence of the catalyst (C2).

In at least one embodiment, compound (A2) is chosen from diorganopolysiloxanes comprising at least two lower (for example C2-C4) alkenyl groups; the lower alkenyl groups may be chosen from vinyl, allyl and propenyl groups. These lower alkenyl groups may be located in any position on the organopolysiloxane molecule, but in at least one embodiment are located at the ends of the organopolysiloxane molecule. The organopolysiloxane (A2) may have a branched-chain, linear-chain, cyclic or network structure. In at least one embodiment, the organopolysiloxane (A2) has a linear-chain structure. Compound (A2) may have a viscosity ranging from the liquid state to the gum state. In at least one embodiment, compound (A2) has a viscosity of at least 100 centistokes at 25° C.

The organopolysiloxanes (A2) may be chosen from methylvinylsiloxanes, methylvinylsiloxane-dimethylsiloxane copolymers, dimethylpolysiloxanes comprising dimethylvinylsiloxy end groups, dimethylsiloxane-methylphenylsiloxane copolymers comprising dimethylvinylsiloxy end groups, dimethylsiloxane-diphenylsiloxane-methylvinylsiloxane copolymers comprising dimethylvinylsiloxy end groups, dimethylsiloxane-methylvinylsiloxane copolymers comprising trimethylsiloxy end groups, dimethylsiloxane-methylphenylsiloxane-methylvinylsiloxane copolymers comprising trimethylsiloxy end groups, methyl(3,3,3-trifluoropropyl)polysiloxanes comprising dimethylvinylsiloxy end groups, and dimethylsiloxane-methyl(3,3,3-trifluoropropyl)siloxane copolymers comprising dimethylvinylsiloxy end groups.

In at least one embodiment of the present disclosure, compound (B2) is chosen from organopolysiloxanes comprising at least two hydrogens bonded to silicon in each molecule and thus may be the crosslinking agent for the compound (A2).

According to at least one embodiment, the sum of the number of ethylenic groups per molecule of compound (A2) and the number of hydrogen atoms bonded to silicon per molecule of compound (B2) is at least 4.

Compound (B2) may be in any molecular structure, such as of linear-chain or branched-chain structure, or cyclic structure.

Compound (B2) may have a viscosity at 25° C. ranging from 1 to 50,000 centistokes, and may have good miscibility with compound (A).

In at least one embodiment, compound (B2) is added in an amount such that the molar ratio between the total amount of hydrogen atoms bonded to silicon in compound (B2) and the total amount of all of the ethylenically unsaturated groups in compound (A2) ranges from 1/1 to 20/1.

Compound (B2) may be chosen from methylhydrogenopolysiloxanes comprising trimethylsiloxy end groups, dimethylsiloxane-methylhydrogenosiloxane copolymers comprising trimethylsiloxy end groups, and dimethylsiloxane-methylhydrogenosiloxane cyclic copolymers.

Compound (C2) is the crosslinking reaction catalyst, and, in at least one embodiment, may be chosen from chloroplatinic acid, chloroplatinic acid-olefin complexes, chloroplatinic acid-alkenylsiloxane complexes, chloroplatinic acid-diketone complexes, platinum black and platinum on a support.

In at least one embodiment, the catalyst (C2) is added in an amount ranging from 0.1 to 1000 parts by weight, such as from 1 to 100 parts by weight, as clean platinum metal per 1000 parts by weight of the total amount of compounds (A2) and (B2).

Other organic groups may be bonded to silicon in the organopolysiloxanes (A2) and (B2) described above, for instance alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Non-emulsifying silicone elastomers according to the present disclosure may be mixed with at least one hydrocarbon-based oil and/or at least one silicone oil to form a gel. In these gels, non-emulsifying elastomers may be in the form of non-spherical particles.

Non-emulsifying elastomers that may be used according to at least one embodiment include those sold under the names KSG-6, KSG-15, KSG-16, KSG-18, KSG-41, KSG42, KSG- 43, KSG-44, USG-105 and USG-106 by the company Shin-Etsu, DC9040, DC9041, DC9509, DC9505, DC9506, DC5930, DC9350, DC9045 and DC9043 by the company Dow Corning, Gransil by the company Grant Industries, and SFE 839 by the company General Electric.

When they are present, the non-emulsifying elastomers may be present in an amount ranging from 0.01% to 10% by weight, such as from 0.5% to 5% or from 1% to 3% by weight, relative to the total weight of the composition.

Oils

According to at least one embodiment, the silicone elastomers according to the present disclosure are mixed with at least one oil (or mixture of oils) and form an oily gel.

The at least one oil may be chosen from volatile oils and non-volatile oils, and mixtures thereof.

The composition according to the present disclosure may comprise at least one volatile oil.

For the purposes of the present disclosure, the term "volatile oil" means any oil that is capable of evaporating on contact with the skin, at room temperature and atmospheric pressure. Volatile oils according to the present disclosure are volatile cosmetic oils that are liquid at room temperature, with a non-zero vapor pressure at room temperature and atmospheric pressure, which may range, for example, from 0.13 Pa to 40,000 Pa (0.001 to 300 mmHg) or from 1.3 Pa to 1300 Pa (0.01 to 10 mmHg).

The volatile oils may be chosen from volatile hydrocarbon-based oils, volatile silicone oils and volatile fluoro oils, and mixtures thereof.

In the present disclosure, the term "hydrocarbon-based oil" means an oil mainly comprising hydrogen and carbon atoms and optionally oxygen, nitrogen, sulfur and/or phosphorus atoms.

The volatile hydrocarbon-based oils may be chosen from hydrocarbon-based oils comprising from 8 to 16 carbon atoms, such as, for example, branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade names Isopar® and Permethyl®.

Volatile oils that may also be used according to at least one embodiment include volatile silicones, for instance volatile linear or cyclic silicone oils, for example, those with a viscosity ≤5 centistokes (5×$10^{-6}$ $m^2$/s) and may comprise from 2 to 10 silicon atoms, such as from 2 to 7 silicon atoms, these silicones optionally comprising alkyl or alkoxy groups comprising from 1 to 10 carbon atoms. As volatile silicone oils that may be used in at least one embodiment of the present disclosure, non-limiting mention may be made of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The volatile fluoro oil generally does not have a flash point.

Among volatile fluoro oils that may be used according to at least one embodiment of the present disclosure, non-limiting mention may be made of nonafluoroethoxybutane, nonafluoromethoxybutane, decafluoropentane, tetradecafluorohexane and dodecafluoropentane, and mixtures thereof.

The volatile oils may be present in the composition in an amount ranging from 1% to 50% by weight, relative to the total weight of the composition, such as, for example, from 5% to 30% by weight or from 7% to 20% by weight, relative to the total weight of the composition.

The composition according to the present disclosure may comprise at least one non-volatile oil.

In the context of the present disclosure, the term "non-volatile oil" means an oil that remains on the skin at room temperature and atmospheric pressure for at least several hours and that, in at least one embodiment, has a vapor pressure of less than 0.13 Pa (0.01 mmHg).

These non-volatile oils may be hydrocarbon-based oils, such as, for example, of animal or plant origin, or silicone oils, or mixtures thereof. In the present disclosure, the term "hydrocarbon-based oil" means an oil mainly comprising hydrogen and carbon atoms and optionally oxygen, nitrogen, sulfur and/or phosphorus atoms.

In at least one embodiment, the non-volatile oils are chosen from non-volatile hydrocarbon-based oils, which may be fluorinated, and non-volatile silicone oils.

Among non-volatile hydrocarbon-based oils that may be used according to at least one embodiment, non-limiting mention may be made of:

hydrocarbon-based oils of animal origin, hydrocarbon-based oils of plant origin, such as triglycerides consisting of fatty acid esters of glycerol, the fatty acids of which may have varied chain lengths from $C_4$ to $C_{24}$, these chains being linear or branched, and saturated or unsaturated; in at least one embodiment, these oils may be chosen from heptanoic and octanoic acid triglycerides, wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, sesame seed oil, marrow oil, rapeseed oil, blackcurrant oil, evening primrose oil, millet oil, barley oil, quinoa oil, rye oil, safflower oil, candlenut oil, passionflower oil, musk rose oil, shea butter, and caprylic/capric acid triglycerides, for instance those sold by the company Stearineries Dubois or those sold under the names Miglyol 810®, 812® and 818® by the company Dynamit Nobel, synthetic ethers containing from 10 to 40 carbon atoms, linear or branched hydrocarbons of mineral or synthetic origin, such as petroleum jelly, polydecenes, hydrogenated polyisobutene such as Parleam®, squalane and liquid paraffins, and mixtures thereof, synthetic esters, for instance oils of formula $R_1COOR_2$ wherein $R_1$ is chosen from linear and branched fatty acid residues comprising from 1 to 40 carbon atoms and $R_2$ is chosen from hydrocarbon-based chains, which may be branched, comprising from 1 to 40 carbon atoms, on condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, isodecyl neopentanoate, 2-ethylhexyl palmitate, isostearyl isostearate, 2-hexyldecyl laurate, 2-octyldecyl palmitate, 2-octyldodecyl myristate, or alcohol or polyalcohol heptanoates, octanoates, decanoates or ricinoleates, for instance propylene glycol dioctanoate; hydroxylated esters, for instance isostearyl lactate, diisostearyl malate or 2-octyldodecyl lactate; polyol esters and pentaerythritol esters, fatty alcohols that are liquid at room temperature with a branched and/or unsaturated carbon-based chain comprising from 12 to 26 carbon atoms, for instance octyldodecanol, isostearyl alcohol, oleyl alcohol, 2-hexyldecanol, 2-butyloctanol or 2-undecylpentadecanol, higher fatty acids such as oleic acid, linoleic acid or linolenic acid, and mixtures thereof.

Non-volatile silicone oils that may be used in the composition according to at least one embodiment of the disclosure may be chosen from non-volatile polydimethylsiloxanes (PDMS), polydimethylsiloxanes comprising alkyl or alkoxy groups, which are pendent and/or at the end of a silicone chain, these groups each comprising from 2 to 24 carbon atoms, phenyl silicones, for instance phenyl trimethicones, phenyl dimethicones, phenyltrimethylsiloxydiphenylsiloxanes, diphenyl dimethicones and diphenyl-methyldiphenyltrisiloxanes, and mixtures thereof.

The non-volatile oils may be present in the composition in an amount ranging from 1% to 50% by weight, such as, for example, from 5% to 40% by weight or from 10% to 30% by weight, relative to the total weight of the composition.

According to at least one embodiment, the composition comprises at least two silicone oils of different volatility.

In at least one embodiment of the present disclosure, the composition comprises at least one volatile silicone oil and at least one non-volatile silicone oil.

In total, in the composition, the oil (or the mixture of oils) may be present in an amount ranging from 5% to 70% by weight, such as, for example, from 10% to 60% by weight or from 20% to 50% by weight, relative to the total weight of the composition.

Aqueous Phase

The composition according to the disclosure comprises an aqueous phase.

The aqueous phase comprises water. The water may be a floral water such as cornflower water and/or a mineral water such as eau de Vittel, eau de Lucas or eau de La Roche Posay and/or a spring water.

The aqueous phase may also comprise organic solvents that are water-miscible (at room temperature −25° C.), for instance monoalcohols comprising from 2 to 6 carbon atoms, such as ethanol or isopropanol; polyols that, for example, comprise from 2 to 20 carbon atoms, such as those comprising from 2 to 10 carbon atoms or from 2 to 6 carbon atoms, such as glycerol, propylene glycol, butylene glycol, pentylene glycol, hexylene glycol, dipropylene glycol or diethylene glycol; glycol ethers (for example, those containing from 3 to 16 carbon atoms) such as mono-, di- or tripropylene glycol ($C_1$-$C_4$)alkyl ethers or mono-, di- or triethylene glycol ($C_1$-$C_4$)alkyl ethers; and mixtures thereof.

According to at least one embodiment, the water-miscible organic solvents are present in the composition in an amount ranging from 3% to 15% by weight, such as from 5% to 12% by weight, relative to the total weight of the composition.

The aqueous phase may also comprise stabilizers, for example sodium chloride, magnesium dichloride and magnesium sulfate.

The aqueous phase may also comprise any water-soluble or water-dispersible compound that is compatible with an aqueous phase, such as gelling agents, film-forming polymers, thickeners and surfactants, and mixtures thereof.

In at least one embodiment, the aqueous phase is present in the composition in an amount greater than or equal to 25% by weight relative to the total weight of the composition, and less than 50% by weight relative to the total weight of the composition.

In at least one embodiment, water is present in the composition in an amount ranging from 25% to 50% by weight, such as, for example, from 30% to 50% by weight, relative to the total weight of the composition.

According to at least one embodiment, the aqueous phase is present in a content such that the weight ratio of the oily phase to the aqueous phase ranges from 0.5 to 2.5, such as from 0.7 to 2 or from 1 to 2.

Fillers

The composition according to the present disclosure may comprise fillers.

In the context of the present disclosure, the term "fillers" should be understood as meaning colorless or white, mineral or synthetic particles of any form, which are insoluble in the medium of the composition irrespective of the temperature at which the composition is manufactured.

The fillers may be mineral or organic and of any form, platelet-shaped, spherical or oblong, irrespective of the crystallographic form (for example lamellar, cubic, hexagonal, orthorhombic, etc.). Non-limiting mention may be made of talc, mica, silica, kaolin, polyamide (Nylon®) powders, poly-β-alanine powders, polyethylene powders, polyurethane powders such as the powder of the copolymer of hexamethylene diisocyanate and of trimethylol hexyl lactone sold under the name Plastic Powder D-400 by the company Toshiki, tetrafluoroethylene polymer (Teflon®) powders, lauroyllysine, starch, boron nitride, hollow polymer microspheres such as those of polyvinylidene chloride/acrylonitrile, for instance Expancel® (Nobel Industrie), acrylic acid copolymers, silicone resin powders, including silsesquioxane powders (silicone resin powders described, for example, in European Patent No. EP 0 293 795; for example, Tospearls® from Toshiba), elastomeric polyorganosiloxane particles, polymethyl methacrylate particles, precipitated calcium carbonate, magnesium carbonate, magnesium hydrogen carbonate, hydroxyapatite, hollow silica microspheres, glass or ceramic microcapsules, and metal soaps derived from organic carboxylic acids comprising from 8 to 22 carbon atoms, such as from 12 to 18 carbon atoms, for example zinc stearate, magnesium stearate, lithium stearate, zinc laurate or magnesium myristate; barium sulfate, and mixtures thereof.

According to at least one embodiment, the composition according to the present disclosure comprises a spherical filler. The spherical filler may be chosen, for example, from polyamide powders and powders of a copolymer of hexamethylene diisocyanate and of trimethylol hexyl lactone.

In at least one embodiment, the fillers dispersed in the composition are present in an amount ranging from 0.5% to 20% by weight, such as, for example, from 1% to 15% by weight or from 2% to 10% by weight, relative to the total weight of the composition.

Dyestuffs

According to at least one embodiment of the present disclosure, the composition may comprise at least one dyestuff.

For the purposes of the present disclosure, the term "dyestuff" means a compound capable of producing a colored optical effect when it is formulated in sufficient amount in a suitable cosmetic medium.

In at least one embodiment, the at least one dyestuff is chosen from pigments, nacres, flakes, liposoluble dyes and water-soluble dyes, and mixtures thereof.

In the present disclosure, the term "pigments" should be understood as meaning white or colored, mineral or organic particles, which are insoluble in the liquid organic phase and which are intended to color and/or opacify the composition.

The term "nacres", as used in the present disclosure, should be understood as meaning iridescent particles, produced, for instance, by certain molluscs in their shell or else synthesized, which are insoluble in the medium of the composition.

In the context of the present disclosure, the term "dyes" should be understood as meaning generally organic compounds that are soluble in fatty substances such as oils or in an aqueous phase.

In at least one embodiment, the at least one dyestuff is present in an amount ranging from 0.01% to 40% by weight, such as, for example, from 5% to 30% by weight or from 5% to 20% by weight, relative to the total weight of the composition.

According to at least one embodiment of the present disclosure, the at least one dyestuff comprises at least one pigment.

The at least one pigment may be chosen from mineral pigments, organic pigments and composite pigments (i.e. pigments based on mineral and/or organic materials).

In the present disclosure, the term "pigments" should be understood as meaning mineral or synthetic particles of any form, endowed with an optical effect, which are insoluble in the medium of the composition irrespective of the temperature at which the composition is manufactured.

The at least one pigment may be chosen from, for example, monochromatic pigments, lakes, nacres and pigments with an optical effect, for instance reflective pigments and goniochromatic pigments.

In at least one embodiment, the mineral pigments are chosen from metal oxide pigments, mica coated with titanium dioxide, mica coated with bismuth oxychloride, titanium mica coated with iron oxide, titanium mica coated with ferric blue, titanium mica coated with chromium oxide, iron oxides, titanium dioxide, zinc oxides, cerium oxide, zirconium oxide or chromium oxide; manganese violet, Prussian blue, ultramarine blue, ferric blue, bismuth oxychloride, colored nacreous pigments such as titanium mica with iron oxides, titanium mica with, for example, ferric blue or chromium oxide, titanium mica with an organic pigment of the abovementioned type, and also nacreous pigments based on bismuth oxychloride, and mixtures thereof.

The organic pigments may be, for example:
cochineal carmine;
organic pigments of azo dyes, anthraquinone dyes, indigoid dyes, xanthene dyes, pyrene dyes, quinoline dyes, triphenylmethane dyes or fluorane dyes;
organic lakes or insoluble salts of sodium, potassium, calcium, barium, aluminium, zirconium, strontium or titanium, or of acidic dyes such as azo dyes, anthraquinone dyes, indigoid dyes, xanthene dyes, pyrene dyes, quinoline dyes, triphenylmethane dyes or fluorane dyes. These dyes may comprise at least one carboxylic or sulfonic acid group;
melanin pigments.

Among the organic pigments that may be used according to the present disclosure, non-limiting mention may be made of D&C Blue No 4, D&C Brown No 1, D&C Green No 5, D&C Green No 6, D&C Orange No 4, D&C Orange No 5, D&C Orange No 10, D&C Orange No 11, D&C Red No 6, D&C Red No 7, D&C Red No 17, D&C Red No 21, D&C Red No 22, D&C Red No 27, D&C Red No 28, D&C Red No 30, D&C Red No 31, D&C Red No 33, D&C Red No 34, D&C Red No 36, D&C Violet No 2, D&C Yellow No 7, D&C Yellow No 8, D&C Yellow No 10, D&C Yellow No 11, FD&C Blue No 1, FD&C Green No 3, FD&C Red No 40, FD&C Yellow No 5 and FD&C Yellow No 6.

According to at least one embodiment, the at least one pigment present in the composition according to the disclosure is chosen from hydrophobic-coated pigments.

In the context of the present disclosure, the term "hydrophobic-coated pigments" means pigments surface-treated with a hydrophobic agent to make them compatible with the fatty phase of the emulsion, in order that they may show good wettability with the oils of the fatty phase. These treated pigments may be well dispersed in the fatty phase.

The pigments intended to be coated may be mineral or organic pigments described above.

In at least one embodiment, iron oxide or titanium dioxide pigments are used.

The hydrophobic-treatment agent may be chosen from silicones, for instance methicones, dimethicones or perfluoroalkylsilanes; fatty acids, for instance stearic acid; metal soaps, for instance aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups, and amino acids; N-acylamino acids or salts thereof; lecithin, isopropyl triisostearyl titanate, and mixtures thereof.

The N-acylamino acids may comprise an acyl group comprising from 8 to 22 carbon atoms, for instance a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine.

In the present disclosure, the term "alkyl" mentioned in the compounds mentioned above may denotes an alkyl group comprising from 1 to 30 carbon atoms, such as from 5 to 16 carbon atoms.

Hydrophobic-treated pigments are described, for example, in European Patent Application No. EP-A-1 086 683.

The pigments may be present in the composition according to at least one embodiment of the present disclosure in an amount ranging from 2% to 40% by weight, such as from 5% to 30% by weight or from 5% to 20% by weight, relative to the total weight of the composition.

The liposoluble dyes may be chosen from, for example, Sudan Red, D&C Red No. 17, D&C Green No. 6, β-carotene, soybean oil, Sudan Brown, D&C Yellow No. 11, D&C Violet No. 2, D&C Orange No. 5, quinoline yellow, annatto and bromo acids.

The water-soluble dyes may be chosen from, for example, beetroot juice, methylene blue and caramel.

Additives

The composition according to the present disclosure may comprise at least one additional cosmetic ingredient, which may be chosen from, for example, hydrophilic or lipophilic gelling agents and/or thickeners, antioxidants, fragrances, preserving agents, neutralizers, sunscreens, vitamins, moisturizers, self-tanning compounds, anti-wrinkle active agents, emollients, hydrophilic or lipophilic active agents, anti-pollution agents or free-radical scavengers, sequestrants, film-forming agents, non-elastomeric surfactants, dermo-relaxing active agents, calmatives, agents for stimulating the synthesis and/or for preventing the degradation of dermal or epidermal macromolecules, anti-glycation agents, anti-irritant agents, desquamating agents, depigmenting agents, anti-pigmenting or pro-pigmenting agents, NO-synthase inhibitors, agents for stimulating fibroblast or keratinocyte proliferation and/or keratinocyte differentiation, agents acting on the capillary circulation, agents acting on the energy metabolism of cells, and cicatrizing agents, and mixtures thereof.

According to at least one embodiment, the composition according to the present disclosure has a viscosity ranging from 10 to 300 Pa·s for a shear of $1\ s^{-1}$, such as, for example, from 15 to 200 Pa·s for a shear of $1\ s^{-1}$.

The viscosity of the composition is measured using a RheoStress RS 600 controlled-stress rheometer from the company Thermo. The measurement is performed at 25° C. using a sanded, 2° angle, 60 mm plate cone with a 0.105 mm gap.

The present disclosure is illustrated in greater detail in the examples that follow.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The examples that follow serve to illustrate the present disclosure without, however, being limiting in nature.

EXAMPLE 1

Foundation

A foundation having the composition below was prepared:

| | |
|---|---|
| Polyglycerolated emulsifying silicone elastomer at 25% by weight in polydimethylsiloxane (6 cSt) (1) | 13 wt. % |
| Polyoxyalkylenated emulsifying silicone elastomer at 25% by weight in polydimethylsiloxane (6 cSt) (2) | 10 wt. % |
| Cyclopentadimethylsiloxane (3) | 11 wt. % |
| Phenyl trimethicone (4) | 9 wt. % |
| Pigments | 8 wt. % |
| Nylon 12 powder (5) | 3 wt. % |
| Propylene glycol | 1 wt. % |
| Glycerol | 6 wt. % |
| Magnesium sulfate | 1 wt. % |
| Preserving agent | qs |
| Water | qs |

(1) KSG-710 from the company Shin-Etsu
(2) KSG-210 from the company Shin-Etsu
(3) Dow Corning 245 Fluid from the company Dow Corning
(4) Dow Corning 556 Cosmetic Grade Fluid from the company Dow Corning
(5) Orgasol 2002 Exd Nat Cos 204 from the company Arkema Preparation Method:

The polyglycerolated emulsifying silicone elastomer, the polyoxyalkylenated emulsifying silicone elastomer, the polydimethylsiloxane, the cyclopentadimethylsiloxane, the phenyl trimethicone, the pigments and the Nylon 12 powder were mixed together (phase A).

Separately, the propylene glycol, the glycerol, the magnesium sulfate, the preserving agents and the water were mixed together (phase B).

Phase B was poured into phase A to form the emulsion.

The foundation obtained had a creamy texture and spread easily on the skin, giving a soft, fondant feel.

| | |
|---|---|
| Polyglycerolated emulsifying silicone elastomer at 25% by weight in polydimethylsiloxane (6 cSt) (1) | 13 wt. % |
| Polyoxyalkylenated emulsifying silicone elastomer at 25% by weight in polydimethylsiloxane (6 cSt) (2) | 9 wt. % |
| Cyclopentadimethylsiloxane (3) | 13 wt. % |
| Phenyl trimethicone (4) | 6 wt. % |
| Pigments | 12 wt. % |
| Nylon 12 powder (5) | 3 wt. % |
| Propylene glycol | 2 wt. % |
| Glycerol | 5 wt. % |
| Magnesium sulfate | 1 wt. % |
| Preserving agent | qs |
| Water | qs |

(1) KSG-710 from the company Shin-Etsu
(2) KSG-210 from the company Shin-Etsu
(3) Dow Corning 245 Fluid from the company Dow Corning
(4) Dow Corning 556 Cosmetic Grade Fluid from the company Dow Corning
(5) Orgasol 2002 Exd Nat Cos 204 from the company Arkema

EXAMPLE 2

Foundation

A foundation having the composition below was prepared:
The preparation method was the same as that of Example 1.
The foundation obtained had a creamy texture and spread easily on the skin, giving a soft, fondant feel.

EXAMPLE 3

Foundation

A foundation having the composition below was prepared:

| | |
|---|---|
| Polyglycerolated emulsifying silicone elastomer at 25% by weight in polydimethylsiloxane (6 cSt) (1) | 8.5 wt. % |
| Polyoxyalkylenated emulsifying silicone elastomer at 25% by weight in polydimethylsiloxane (6 cSt) (2) | 10 wt. % |
| Oxyethylenated polydimethylsiloxane (3) | 2 wt. % |
| Cyclopentadimethylsiloxane (4) | 17 wt. % |
| Polydimethylsiloxane (5 cSt) (5) | 5 wt. % |
| Pigments | 12 wt. % |
| Powder of a copolymer of hexamethylene diisocyanate and of trimethylol hexyl lactone (6) | 3 wt. % |
| Propylene glycol | 2 wt. % |
| Glycerol | 5 wt. % |
| Magnesium sulfate | 1 wt. % |
| Preserving agent | qs |
| Water | qs |

(1) KSG-710 from the company Shin-Etsu
(2) KSG-210 from the company Shin-Etsu
(3) KF-6017 from the company Shin-Etsu
(4) Dow Corning 245 Fluid from the company Dow Corning
(5) Dow Corning Fluid 200 5 cs from the company Dow Corning
(6) Plastic Powder D-400 from the company Toshiki Preparation Method:

The polyglycerolated emulsifying silicone elastomer, the polyoxyalkylenated emulsifying silicone elastomer, the polydimethylsiloxane, the cyclopentadimethylsiloxane, the oxyethylenated polydimethylsiloxane, the pigments and the Nylon 12 powder were mixed together (phase A).

Separately, the propylene glycol, the glycerol, the magnesium sulfate, the preserving agents and the water were mixed together (phase B).

Phase B was poured into phase A to form the emulsion.

The foundation obtained had a creamy texture and spread easily on the skin, giving a soft, fondant feel.

What is claimed is:

1. A cosmetic composition in the form of a water-in-oil emulsion comprising at least two different emulsifying silicone elastomers, wherein the at least two different emulsifying silicone elastomers are present in the composition in an amount ranging from 4% to 7% by weight relative to the total weight of the composition, and wherein one of the at least two different emulsifying silicone elastomers is chosen from polyglycerolated silicone elastomers and another of the at least two different emulsifying silicone elastomers is chosen from polyoxyalkylenated silicone elastomers.

2. The composition according to claim 1, wherein each emulsifying silicone elastomer is present in the composition in an amount greater than 1.5% by weight, relative to the total weight of the composition.

3. The composition according to claim 1, wherein the polyoxyalkylenated silicone elastomers are obtained by a crosslinking addition reaction of a diorganosiloxane comprising at least one hydrogen bonded to silicon and a polyoxyalkylene comprising at least two ethylenically unsaturated groups.

4. The composition according to claim 1, wherein the polyglycerolated silicone elastomers are obtained by a crosslinking addition reaction of a diorganosiloxane comprising at least one hydrogen bonded to silicon and a polyglycerolated compound comprising ethylenically unsaturated groups.

5. The composition according to claim 4, wherein the crosslinking addition reaction takes place in the presence of a platinum catalyst.

6. The composition according to claim 1, wherein the polyglycerolated silicone elastomer(s) are present in an amount of at least 1.5% by weight, relative to the total weight of the composition.

7. The composition according to claim 6, wherein the polyglycerolated silicone elastomer(s) are present in an amount ranging from 1.5% to 5% by weight, relative to the total weight of the composition.

8. The composition according to claim 1, wherein the polyoxyalkylenated silicone elastomer(s) are present in an amount of at least 1.5% by weight, relative to the total weight of the composition.

9. The composition according to claim 8, wherein the polyoxyalkylenated silicone elastomer(s) are present in an amount ranging from 1.5% to 5% by weight, relative to the total weight of the composition.

10. The composition according to claim 1, further comprising at least one oil chosen from hydrocarbon-based oils and silicone oils.

11. The composition according to claim 1, further comprising at least one volatile oil.

12. The composition according to claim 11, wherein the at least one volatile oil is chosen from hydrocarbon-based volatile oils, silicone volatile oils and fluoro volatile oils.

13. The composition according to claim 11, wherein the at least one volatile oil is present in an amount ranging from 1% to 50% by weight, relative to the total weight of the composition.

14. The composition according to claim 13, wherein the at least one volatile oil is present in an amount ranging from 7% to 20% by weight, relative to the total weight of the composition.

15. The composition according to claim 1, further comprising at least one non-volatile oil.

16. The composition according to claim 15, wherein the at least one non-volatile oil is present in an amount ranging from 1% to 50% by weight, relative to the total weight of the composition.

17. The composition according to claim 16, wherein the at least one non-volatile oil is present in an amount ranging from 10% to 30% by weight, relative to the total weight of the composition.

18. The composition according to claim 1, further comprising at least one oil chosen from volatile oils and non-volatile oils, wherein the at least one oil is present in an amount ranging from 5% to 70% by weight, relative to the total weight of the composition.

19. The composition according to claim 18, wherein the at least one oil is present in an amount ranging from 20% to 50% by weight, relative to the total weight of the composition.

20. The composition according to claim 1, further comprising an aqueous phase present in an amount ranging from 25% to 50% by weight, relative to the total weight of the composition.

21. The composition according to claim 20, wherein the aqueous phase is present in an amount ranging from 30% to 50% by weight, relative to the total weight of the composition.

22. The composition according to claim 1, further comprising at least one water-miscible organic solvent.

23. The composition according to claim 22, wherein the at least one water-miscible organic solvent is chosen from polyols and glycol esters.

24. The composition according to claim 22, wherein the at least one water-miscible organic solvent is present in an amount of at least 3% by weight, relative to the total weight of the composition.

25. The composition according to claim 22, wherein the at least one water-miscible organic solvent is present in an amount ranging from 5% to 12% by weight, relative to the total weight of the composition.

26. The composition according to claim 1, wherein the composition comprises an oily phase and an aqueous phase, wherein the weight ratio of the oily phase to the aqueous phase ranges from 0.5 to 2.5.

27. The composition according to claim 26, wherein the weight ratio of the oily phase to the aqueous phase ranges from 1 to 2.

28. The composition according to claim 1, further comprising at least one filler.

29. The composition according to claim 28, wherein the at least one filler is chosen from mineral and organic fillers, in platelet, spherical or oblong form.

30. The composition according to claim 29, wherein the at least one filler is chosen from spherical fillers.

31. The composition according to claim 28, wherein the at least one filler is present in an amount ranging from 0.5% to 20% by weight, relative to the total weight of the composition.

32. The composition according to claim 31, wherein the at least one filler is present in an amount ranging from 2% to 10% by weight, relative to the total weight of the composition.

33. The composition according to claim 1, further comprising at least one dyestuff chosen from pigments, nacres, flakes, liposoluble dyes and water-soluble dyes.

34. The composition according to claim 33, wherein said at least one dyestuff is chosen from at least one pigment.

35. The composition according to claim 34, wherein the at least one pigment is chosen from coated pigments.

36. The composition according to claim 35, wherein the at least one coated pigment is chosen from iron oxide and titanium dioxide pigments.

37. The composition according to claim 33, wherein the at least one dyestuff is present in an amount ranging from 0.01% to 40% by weight, relative to the total weight of the composition.

38. The composition according to claim 37, wherein the at least one dyestuff is present in an amount ranging from 5% to 20% by weight, relative to the total weight of the composition.

39. The composition according to claim 1, further comprising at least one non-emulsifying elastomer.

40. The composition according to claim 39, wherein the at least one non-emulsifying elastomer is present in an amount ranging from 0.01% to 10% by weight, relative to the total weight of the composition.

41. The composition according to claim 40, wherein the at least one non-emulsifying elastomer is present in an amount ranging from 1% to 3% by weight, relative to the total weight of the composition.

42. The composition according to claim 1, wherein the composition has a viscosity ranging from 10 Pa·s to 300 Pa·s for a shear of 1 s$^{-1}$.

43. The composition according to claim 42, wherein the composition has a viscosity ranging from 15 Pa·s to 200 Pa·s for a shear of 1 s$^{-1}$.

44. The composition according to claim 1, further comprising at least one cosmetic ingredient chosen from non-elastomeric surfactants, hydrophilic or lipophilic gelling agents and/or thickeners, antioxidants, fragrances, preserving agents, neutralizers, sunscreens, vitamins, moisturizers, self-tanning compounds, anti-wrinkle active agents, emollients, hydrophilic or lipophilic active agents, anti-pollution agents or free-radical scavengers, sequestrants, film-forming agents, dermo-relaxing active agents, calmatives, agents for stimulating the synthesis and/or for preventing the degradation of dermal or epidermal macromolecules, anti-glycation agents, anti-irritant agents, desquamating agents, depigmenting agents, anti-pigmenting or pro-pigmenting agents, NO-synthase inhibitors, agents for stimulating fibroblast or keratinocyte proliferation and/or keratinocyte differentiation, agents acting on the capillary circulation, agents acting on the energy metabolism of cells, and cicatrizing agents.

45. A cosmetic composition in the form of a water-in-oil emulsion comprising:
   i) at least 1.5% by weight, relative to the total weight of the composition, of a polyoxyalkylenated emulsifying silicone elastomer;
   ii) at least 1.5% by weight, relative to the total weight of the composition, of a polyglycerolated emulsifying silicone elastomer;
   iii) at least 20% by weight, relative to the total weight of the composition, of water;
   iv) at least one volatile oil;
   v) at least 5% by weight, relative to the total weight of the composition, of at least one water-miscible organic solvent chosen from glycols and polyols; and
   vi) at least 5% by weight, relative to the total weight of the composition, of at least one dyestuff,
wherein the composition has a viscosity ranging from 10 Pa·s to 300 Pa·s for a shear of 1 s$^{-1}$, and wherein the polyoxyalkylenated emulsifying silicone elastomer and the polyglycerolated emulsifying silicone elastomer are present in the composition in an amount ranging from 4% to 7% by weight, relative to the total weight of the composition.

46. A process for making up or caring for keratin materials, comprising: applying to the keratin materials a cosmetic composition in the form of a water-in-oil emulsion comprising at least two different emulsifying silicone elastomers, wherein the at least two different emulsifying silicone elastomers are present in the composition in an amount ranging from 4% to 7% by weight relative to the total weight of the composition, and wherein one of the at least two different emulsifying silicone elastomers is chosen from polyglycerolated silicone elastomers and another of the at least two different emulsifying silicone elastomers is chosen from polyoxyalkylenated silicone elastomers.

47. A process for making a makeup composition that is comfortable to wear, has no tacky feel, and/or spreads easily, said process comprising:
   adding to said composition at least two different emulsifying silicone elastomers, wherein the at least two different emulsifying silicone elastomers are present in the composition in an amount ranging from 4% to 7% by weight relative to the total weight of the composition, and wherein said composition is in the form of a water-in-oil emulsion, and wherein one of the at least two different emulsifying silicone elastomers is chosen from polyglycerolated silicone elastomers and another of the at least two different emulsifying silicone elastomers is chosen from polyoxyalkylenated silicone elastomers.

48. A cosmetic composition in the form of a water-in-oil emulsion comprising at least one polyoxyalkylenated emulsifying silicone elastomer formed from divinyl compounds and at least one polyglycerolated emulsifying silicone elastomer and at least one filler, wherein the at least one polyoxyalkylenated emulsifying silicone elastomer formed from divinyl compounds and at least one polyglycerolated emulsifying silicone elastomer together are present in the composition in an amount of at least 3% by weight relative to the total weight of the composition.

49. The composition according to claim 1, wherein the composition is free of hydrophobically treated metal oxides or pigments.

* * * * *